(12) United States Patent
Joseph

(10) Patent No.: US 11,464,683 B2
(45) Date of Patent: Oct. 11, 2022

(54) DISPOSABLE BABY CHANGING PAD SYSTEM AND METHOD OF MAKING THE SAME

(71) Applicant: Matthew Joseph, Aledo, TX (US)

(72) Inventor: Matthew Joseph, Aledo, TX (US)

( * ) Notice: Subject to any disclaimer, the term of this patent is extended or adjusted under 35 U.S.C. 154(b) by 502 days.

(21) Appl. No.: 16/436,490

(22) Filed: Jun. 10, 2019

(65) Prior Publication Data
US 2020/0383847 A1  Dec. 10, 2020

(51) Int. Cl.
| A61F 13/551 | (2006.01) |
| A47D 15/00 | (2006.01) |
| B65F 1/00 | (2006.01) |
| A61F 13/15 | (2006.01) |

(52) U.S. Cl.
CPC .......... *A61F 13/5512* (2013.01); *A47D 15/00* (2013.01); *A61F 13/15723* (2013.01); *A61F 13/5511* (2013.01); *A61F 13/5519* (2013.01); *A61F 13/55115* (2013.01); *B65F 1/0006* (2013.01); *A61F 2013/55195* (2013.01); *B65F 2240/132* (2013.01)

(58) Field of Classification Search
CPC ............ A61F 13/5511; A61F 13/55115; A61F 13/5512; A61F 13/5519; A61F 2013/15073; A61F 2013/55125; A61F 2013/55195; A47D 15/00
See application file for complete search history.

(56) References Cited

U.S. PATENT DOCUMENTS

| 4,964,859 A * | 10/1990 | Feldman | A61F 13/551 206/223 |
| 5,304,158 A * | 4/1994 | Webb | A61F 13/551 604/385.13 |
| 5,582,605 A * | 12/1996 | Lepie | A61F 13/551 206/438 |
| 5,706,950 A * | 1/1998 | Houghton | A61F 13/84 206/581 |
| 7,749,209 B1 * | 7/2010 | Vuckovic | A61F 13/5519 604/385.19 |
| 8,051,510 B2 * | 11/2011 | Soloway | A47D 5/006 5/417 |
| 8,936,154 B2 * | 1/2015 | Booch | B65D 71/063 206/494 |
| 2005/0173292 A1 * | 8/2005 | Klose | A61F 13/55115 206/581 |
| 2012/0311788 A1 * | 12/2012 | Jackson, II | A47D 5/006 5/655 |

* cited by examiner

*Primary Examiner* — Catharine L Anderson
(74) *Attorney, Agent, or Firm* — Leavitt Eldredge Law Firm

(57) ABSTRACT

A disposable baby changing pad system includes a changing pad body extending from a top end to a bottom end and being composed of a thin, flexible material, the changing pad body further having a pocket formed on a top surface of the changing pad body, the pocket having a top layer sealing an interior area of the pocket; an opening extending into the interior area from the top layer; one or more wipes sealed within the pocket; and a diaper positioned on the top surface of the changing pad body; the changing pad body folds around the pocket and the diaper.

6 Claims, 4 Drawing Sheets

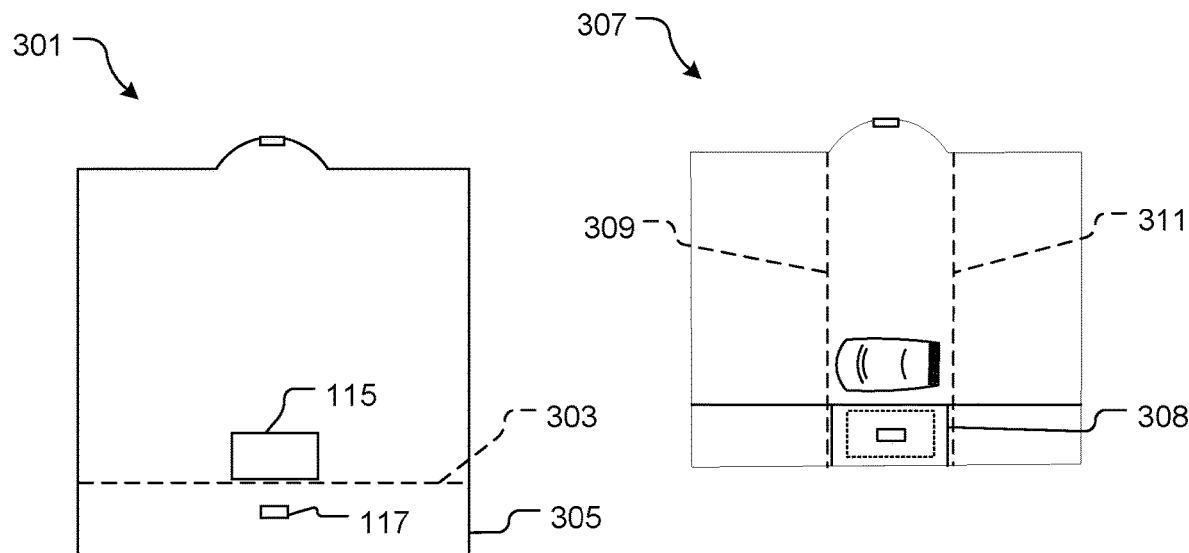
FIG. 3A
FIG. 3B
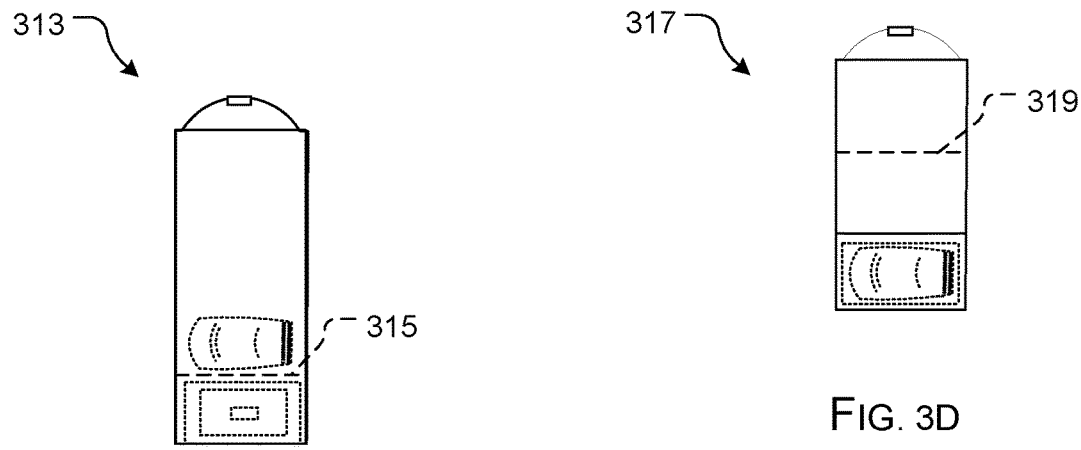
FIG. 3C
FIG. 3D
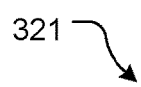
FIG. 3E

DISPOSABLE BABY CHANGING PAD SYSTEM AND METHOD OF MAKING THE SAME

BACKGROUND

1. Field of the Invention

The present invention relates generally to baby changing stations and pads, and more specifically, to a disposable baby changing pad, diaper, and wipes, conveniently packaged into one unit for easy use.

2. Description of Related Art

Baby changing systems are well known in the art and are effective means to assist parents in changing baby diapers. Conventional systems include changing tables located in public restrooms and washable changing pads that parents can carry with them, as well as diapers, and wipes. Parents will commonly carry an entire diaper bag with them to ensure that they have everything they need, including a changing mat, a plurality of diapers, and wipes.

One of the problems commonly associated with conventional changing systems is the bulk of supplies required. Parents may find it cumbersome and inefficient to carry an entire bag full of supplies, particularly when the parent knows they may only need one diaper change on an outing.

Accordingly, although great strides have been made in the area of changing systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIGS. 3A-3E are top views of the method of making and configuration of the system of FIG. 1;

Figure 1:
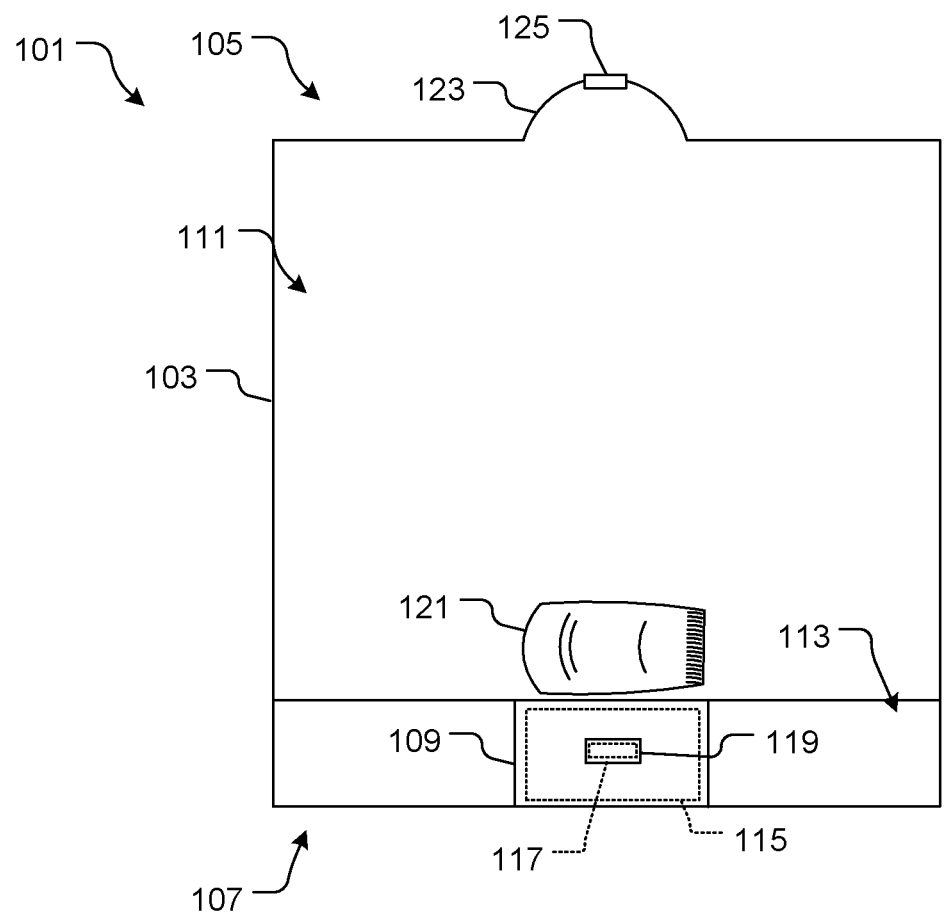
FIG. 1 is a top view of a disposable baby changing pad system in accordance with a preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional changing systems. Specifically, the present invention provides for a compact, disposable changing pad, diaper, and wipe combination that provides for easy changing on the go with limited supplies for parents to keep with them. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a disposable baby changing system 101 in accordance with a preferred embodiment of the present application. It will be appreciated that system 101 overcomes one or more of the above-listed problems commonly associated with conventional baby changing systems.

In the contemplated embodiment, system 101 includes a changing pad body 103 which extends from a top end 105 to a bottom end 107 and is composed of a flexible, thin material, such as a plastic or the like, thereby allowing for the body 103 to be compact. The changing pad body 103 further includes a pocket 109 that is sealed between the top surface 111 and a top layer 113, the pocket 109 configured to hold one or more wipes 115 therein. In the preferred embodiment, the pocket is sealed with watertight materials to prevent leakage of the wipes. In addition, it should be appreciated that the entire changing pad body can be waterproof. It should be appreciated that the system can be configured with a limited number of wipes, such as three, for ensuring the system remains compact. In the preferred embodiment, an opening 117 is cut through the top layer 113 to provide access to the one or more wipes, and in some embodiments, a sticker 119 is secured over the opening.

In an alternative embodiment, it is contemplated that the wipes can be contained in a wipe package, wherein the package itself is folded up with the changing pad body into a compact configuration for travel. In yet another alternative embodiment, the wipes are merely secured to the changing pad, such as through an adhesive or the like.

System 101 further includes a diaper 121, wherein the diaper 121 is positioned over the top surface 111. It should be appreciated that in the preferred embodiment, only one diaper is used, however, it is contemplated that additional diapers could be secured therein.

Figure 2:
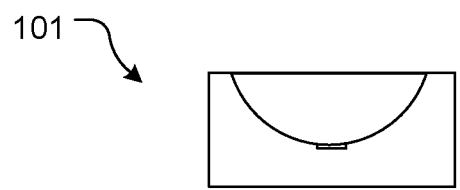
FIG. 2 is a top view of the system of FIG. 1 in a folded configuration.

As shown in FIG. 2, the system is configured to fold around the diaper and the wipes, thereby creating a compact system that can be transported easily. In some embodiments, a tab 123 with an adhesive 125 can be used to secure the system in the folded position. It should be appreciated that the system is designed to be disposable, such that the user will change a baby and then proceed to throw the system away.

It should be appreciated that one of the unique features believed characteristic of the present application is the creation of a disposable diaper pad, with wipes and diaper contained therein.

In FIGS. 3A-3E, the steps of making the system 101 are shown. As shown, step 301 provides for placing the one or more wipes 115 in the desired location and cutting the opening 117 in a lower portion 305 of the body. A first fold line 303 provides for a location to fold the bottom portion 305 over the top of the one or more wipes, thereby creating the top layer over the top of the wipes.

As shown in step 307, the pocket is formed by creating a seal 308 around the adhesives. Additional fold lines 309, 311 provide for the location to fold the body around the wipes and diaper, thereby resulting in the configuration shown in step 313. As shown, additional fold lines 315, 319 are used in steps 313, 317 to result in the completely folded configuration 321.

Figure 4:
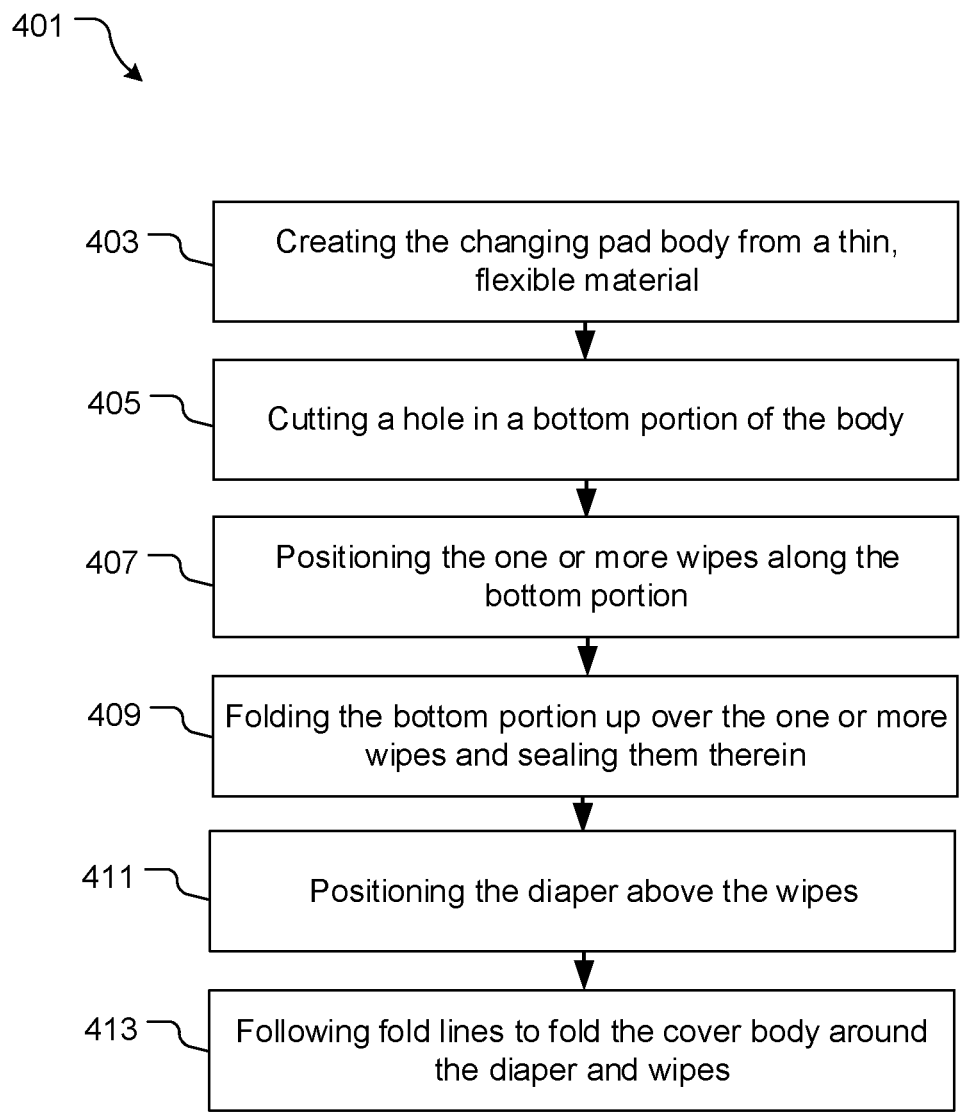
FIG. 4 is a flowchart of the method of making the system of FIG. 1.

In FIG. 4, a flowchart 401 further depicts the steps associated with creating the system 101. As shown, the changing pad body is formed from a thin, flexible material, as shown in box 403. A hole/opening is created in the bottom portion of the body, and the bottom portion is then folded upwards to seal in the one or more wipes into the pocket, as shown with boxes 405, 407, 409. A diaper is positioned above the wipes, and the remaining folding lines are followed to fold the system into the compact configuration, as shown with boxes 411, 413.

Figure 5:
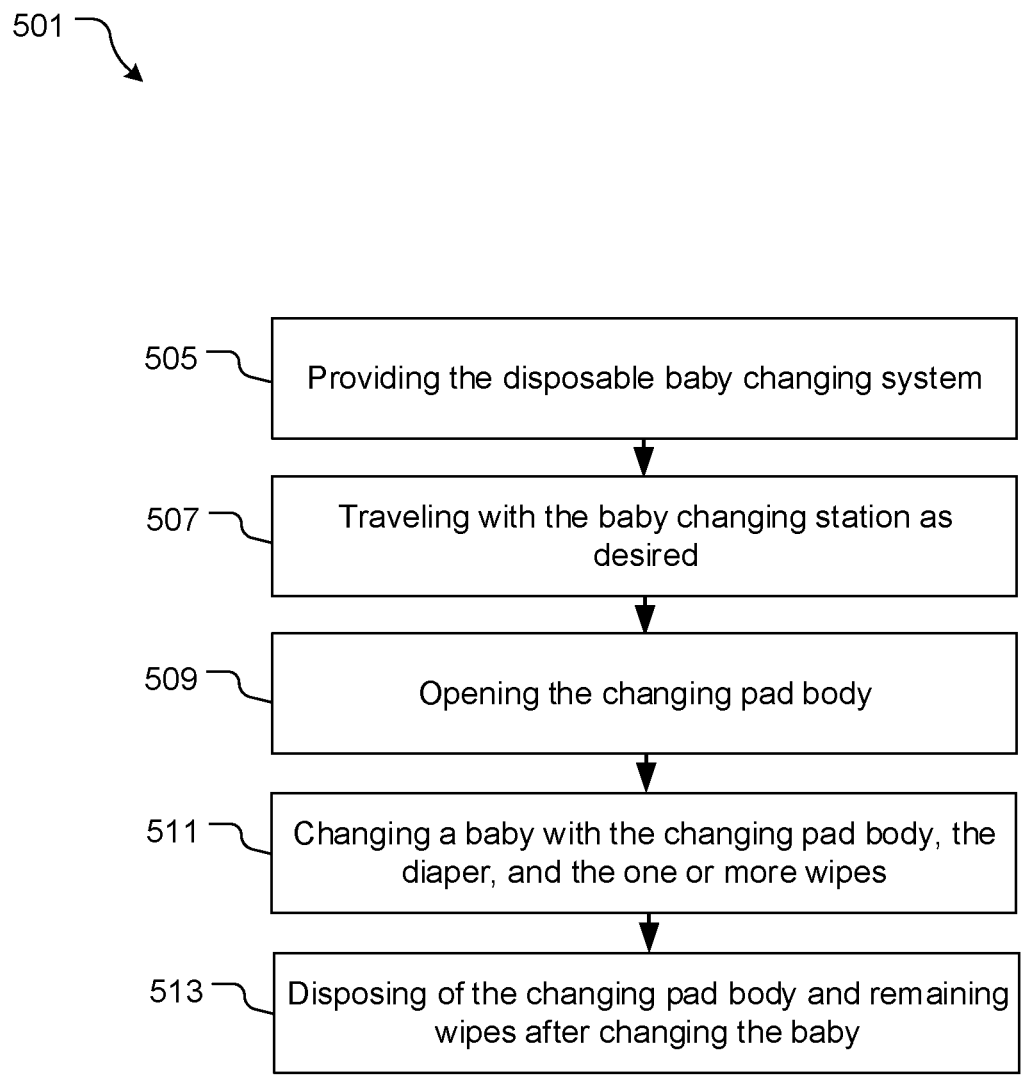
FIG. 5 is a method of use of the system of FIG. 1.

In FIG. 5, a flowchart 501 depicts a method of use of system 101. During use, the system is created and provided, wherein a parent can take the system with them during travels, as shown with boxes 505, 507. The user can then open the changing pad body and proceed to change the baby, using the provided diaper and wipes, as shown with boxes 509, 511. Once completed, the parent can dispose of the changing pad and any remaining wipes, as shown with box 513.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope of the application. Accordingly, the protection sought herein is as set forth in the description. Although the present embodiments are shown above, they are not limited to just these embodiments, but are amenable to various changes and modifications without departing from the spirit thereof.

What is claimed is:

1. A disposable baby changing pad system, comprising:
   a changing pad body extending from a top end to a bottom end and from a first side edge to a second side edge and being composed of a thin, flexible material, the changing pad body having:
   a top surface;
   a top layer secured over a portion of the top surface, the top layer extending from the first side edge to the second side edge; and
   a pocket formed between the top surface and the top layer;
   one or more wipes secured within the pocket; and
   a diaper positioned on the top surface of the changing pad body at a position directly above the pocket;
   a plurality of fold lines for the changing pad body, the plurality of fold lines including:
   a first fold line extending from the top end of the changing pad body to a bottom edge of the pocket on a first side of the diaper and a first side of the one or more wipes;
   a second fold line extending from the top end of the changing pad body to the bottom edge of the pocket on a second side of the diaper and a second side of the one or more wipes;
   a third fold line extending directly above the pocket and below the diaper and extending only between the first fold line and the second fold line such that the third fold line is utilized after folding the first fold line and the second fold line; and
   a fourth fold line and a fifth fold line both extending above the diaper and spaced there apart, the fourth fold line and the fifth fold line utilized to fold the changing pad body after the first, second, and third fold lines are utilized;
   wherein the changing pad body folds around the one or more wipes and the diaper via the plurality of fold lines.

2. The system of claim 1, wherein the changing pad body further comprises:
   the pocket having the top layer sealing an interior area of the pocket with the one or more wipes sealed therein;
   an opening extending into the interior area from the top layer.

3. The system of claim 1, wherein he one or more wipes are three wipes.

4. The system of claim 1, wherein the thin, flexible material is a plastic.

5. A method of making a disposable baby changing system, the method comprising:
   creating a changing pad body out of a thin, flexible material, the changing pad body extending from a top end to a bottom end and from a first side edge to a second side edge;
   positioning one or more wipes on a top surface of the changing pad body;
   cutting a hole through a lower portion of the changing pad body
   sealing a top layer to the top surface to create a pocket, the top layer extending from the first side edge to the second side edge, wherein the one or more wipes are secured within the pocket;
   placing a diaper on the top surface;
   creating a plurality of fold lines for the changing pad body, the plurality of fold lines including a first fold line extending from the top end of the changing pad body to a bottom edge of the pocket on a first side of the diaper and a first side of the one or more wipes, a second fold line extending from the top end of the changing pad body to the bottom edge of the pocket on a second side of the diaper and a second side of the one or more wipes, a third fold line extending directly above the pocket and below the diaper and extending only between the first fold line and the second fold line such that the third fold line is utilized after folding the first fold line and the second fold line, and a fourth fold line and a fifth fold line both extending above the diaper and spaced there apart, the fourth fold line and the fifth fold line utilized to fold the changing pad body after the first, second, and third fold lines are utilized;

following the plurality of fold lines along the changing pad body to fold the changing pad body around the diaper and the pocket.

6. The method of claim 5, further comprising:

securing a sticker over a top of the hole.

\* \* \* \* \*